United States Patent [19]
Nowacki et al.

[11] Patent Number: 5,295,483
[45] Date of Patent: Mar. 22, 1994

[54] LOCATING TARGET IN HUMAN BODY

[76] Inventors: Christopher Nowacki, 1552 Chickamauga, Long Grove, Ill. 60047; Mark T. Horbal, 2 S. 530 Iroquois Courts West, Warrenville, Ill. 60555

[21] Appl. No.: 777,433

[22] Filed: Oct. 11, 1991

Related U.S. Application Data

[63] Continuation of Ser. No. 522,597, May 11, 1990, abandoned.

[51] Int. Cl.⁵ .......................... A61B 8/00; A61B 17/22
[52] U.S. Cl. ................................... 128/660.03; 601/2; 601/4
[58] Field of Search ........ 128/24 AA, 24 EL, 660.03, 128/782, 660.01, 916

[56] References Cited
U.S. PATENT DOCUMENTS 4,896,673 1/1990 Rose et al. ..................... 128/24 EL
5,197,476 3/1993 Nowacki et al. ............... 128/24 EL Primary Examiner—Lee S. Cohen
Assistant Examiner—Krista M. Pfaffle
Attorney, Agent, or Firm—Robert M. Wolters

[57] ABSTRACT

Apparatus and methods are provided for locating a target in a living body. Three cameras are supported at an elevated location such as on a wall or from a ceiling. The cameras are supplied as an integrated unit with a computer and are factory calibrated to said computer. A patient examining table is provided with a single radiation device, the radiation which is detectable by the cameras. The table is moved both horizontally and vertically to establish X, Y and Z coordinates relative to the room in which the installation is made. A hand held ultrasound probe is positioned to detect a target in a body disposed on said table, and an ultrasound scan screen apparatus displays the relation of the probe to the target, and also provides information for moving the table to position the target at a predetermined location.

8 Claims, 2 Drawing Sheets

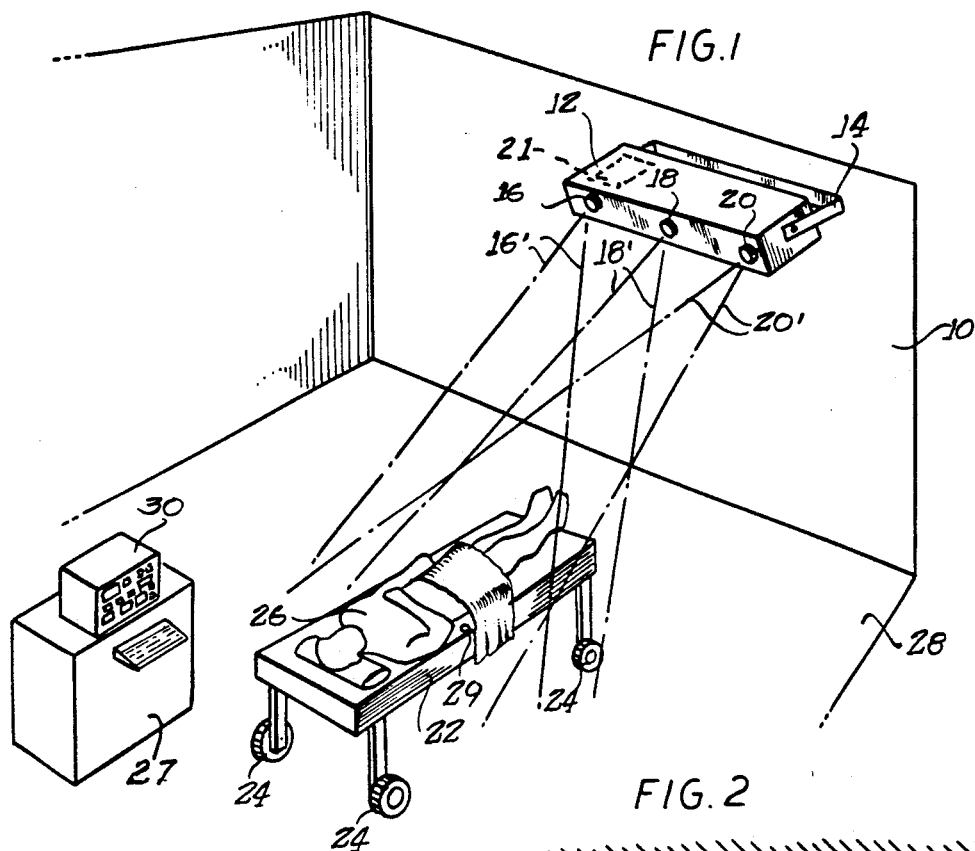
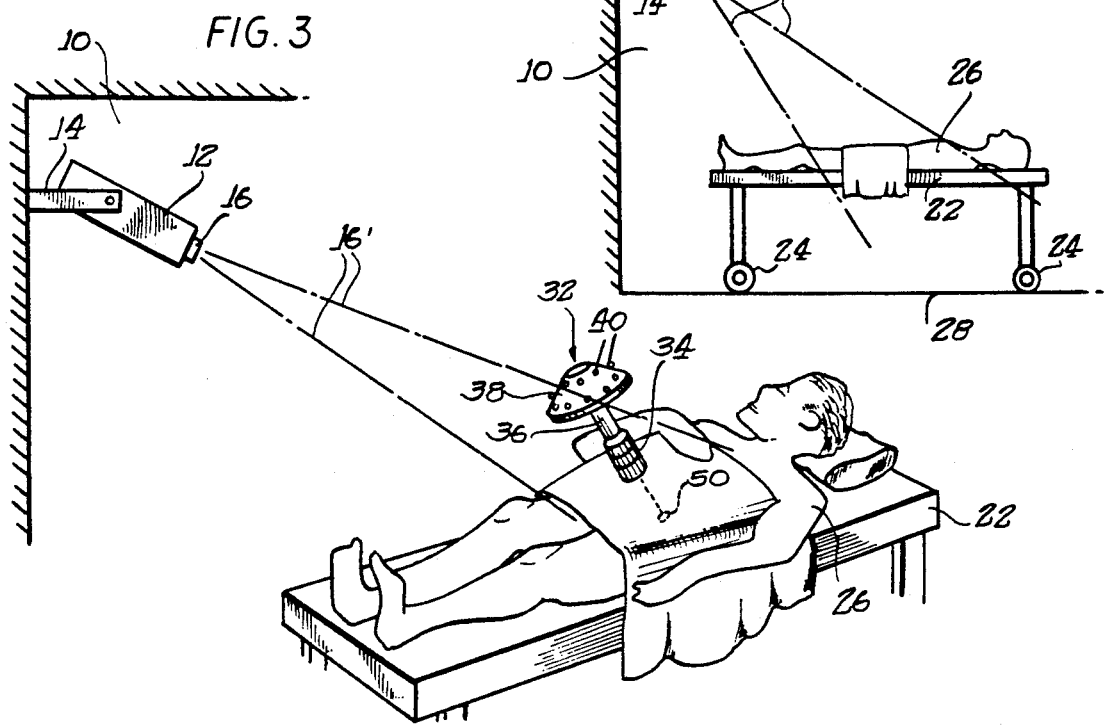

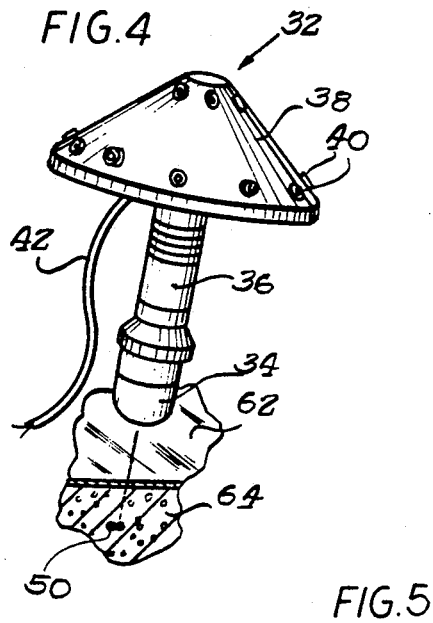

LOCATING TARGET IN HUMAN BODY

RELATED APPLICATIONS

The present application is related to and comprises an improvement on our prior application Ser. No. 07/320,110, filed Mar. 6, 1989, now U.S. Pat. No. 5,197,476 entitled "Locating Target in Human Body". As an improvement, the present invention includes the sequential strobing of the invention described and claimed in U.S. Pat. No. 5,197,476. Furthermore, this application is a continuation of Ser. No. 07/522,597, filed May 11, 1990 now abandoned.

BACKGROUND OF THE INVENTION

Locating targets in the human body by means of ultrasound techniques is well known. In extracorporeal shockwave lithotripsy or disintegration of a concretion or kidney stone in a kidney, ureter, or bladder by means of shockwaves is known. It is the general procedure to use an articulated arm carrying an ultrasonic transducer that both sends out and receives the ultrasound signal. Devices are connected in the articulated arm to indicate the angles between various arm segments, and the angles thereof relative to a base. Movement of such articulated arms is necessarily restricted, and the arms themselves tend to get in the way. The information obtained by such arms and the ultrasound devices carried thereby is fed through a computer to control the position of the lithotripter so that a shockwave generated thereby is focused on the kidney stone or other bodily concretion. Lithotripters have found use in fragmenting or destroying gallstones, as well as kidney stones. It is also sometimes necessary to locate a tumor in the body, or the location of a broken bone to study how well it is mending.

OBJECTS AND ADVANTAGES OF THE PRESENT INVENTION

It is an object of the present invention to provide apparatus utilizing three cameras and a hand-held ultrasound unit cooperating with a computer for the location of targets in the human body, such as concretions, tumors, or mending bones.

It is further an object of the present invention to provide an apparatus as set forth in the previous object in which the three cameras are factory positioned and programmed, and wherein a patient treatment table has to be oriented only once with regard to the cameras.

In our previous and aforesaid U.S. patent application 07/320,110 a pair of cameras were utilized in conjunction with a space frame having a plurality of strobed lights thereon to establish a space or volume in which a human body and a kidney stone or the like were subsequently located. An ultrasonic probe having both a sending and receiving unit, and also having a plurality of strobed lights thereon was subsequently used to locate a kidney stone, and particularly to locate it with regard to the space previously defined by the lights on the frame, which frame has been removed before the patient is placed on the treatment table.

In accordance with the present invention three cameras are used, which are factory mounted in a housing in predetermined relation to one another, the cameras being generally aligned, the outer two having their axes tipped in toward the axis of the center camera. Each camera is optimized for one of three operating planes, and for a particular distance. An auxiliary computer is housed within the housing for the three cameras, and calibration of the cameras relative to one another is included in this computer. The housing is mounted in a treatment room, and a zero point on a patient treatment table is viewed by the cameras as the table is moved about the room, whereby to orient the patient table with respect to the cameras. A more comprehensive or main computer receives the information and stores it with regard to the location of the treatment table relative to the three cameras. Subsequently, a patient is placed on the treatment table, and an ultrasonic probe is used for locating a kidney stone or other suitable or desired target within a human body placed on the treatment table. The location of the stone is then determined by the computer relative to the previously mentioned zero point, and it is then only necessary to move the table to the extent necessary to place the stone or the like at the previously determined zero point.

THE DRAWINGS

The present invention will best be understood from the following specification when taken in connection with the accompanying drawings wherein:

FIG. 1 is a somewhat stylized perspective view showing the apparatus of the present invention in conjunction with a patient treatment table;

FIG. 2 is a side view of the apparatus of FIG. 1;

FIG. 3 is a perspective view on a slightly enlarged scale showing the foregoing apparatus in conjunction with the ultrasonic probe and the strobed lights thereon;

FIG. 4 is a perspective view of the probe as used to locate a bodily concretion or the like; and FIG. 5 is a front view of the ultrasound scan screen used in conjunction with the probe.

DETAILED DISCLOSURE OF THE ILLUSTRATED EMBODIMENT

Referring now in greater detail to the figures of the drawings, and first to FIGS. 1-3, there will be seen a room 10 with a camera unit 12 mounted on the wall or ceiling by means of a bracket 14. The camera unit 12 includes an elongated, rectangular housing in which are mounted three cameras, respectively designated by numerals 16, 18, and 20. Since the cameras are mounted completely within the housing, the only portions thereof that show are the lenses that extend through the front. The center lens 18 is aimed substantially straight ahead, while the two side lenses 16 and 20 converge generally toward the center as can be seen with reference to the pairs of broken lines 16', 18' and 20' respectively indicating the aspect of each camera. The two outer cameras and their lenses 16 and 20 are angled in about 10°-15° toward the center camera and its lens 18. The cameras are respectively concentrated on one plane, one on the x-y plane, one the x-z plane, and one on the the y-z plane. The cameras are prefocused to provide good resolution at one and one-half to four meters. A small computer is also housed within the housing of the camera unit 12, and the cameras are factory calibrated with the calibration entered into the computer in the housing. The small computer 21 strobes the infrared lights on the probe, and also the cameras.

In addition, there is a patient treatment table 22 which is mounted on wheels 24 for movement about the room. Such movement can be entirely manual or it can be effected mechanically or electrically. The table also will rise and fall vertically. Such tables are known, and the table 22 therefore is shown only schematically in the present drawings. It will be understood that the table also is cut away to expose the area of the body of the patient 26 at which the kidney or other portion of the body to be studied is located, so that a lithotripter reflector or other suitable mechanism can be raised up beneath the body. It will be understood that the wheels 24 rest on and are capable of moving about on the floor 28 of the room 10. For initial calibration of the camera apparatus relative to a particular room, a radiation source comprising a light is provided on the table at a known position 29 relative to a zero point. This zero point typically is the position where a kidney stone is to be disintegrated, or other target is to be located in the body. The light can be precisely on the zero point for convenience, or it can be in any known relation to the zero point. The cameras 16, 18 and 20 are primarily sensitive to infrared light, and the light thus conveniently can be an infrared light emitting diode (LED). The table is then moved about the floor in the x-y or horizontal plane in both x and y directions. The table is also moved up and down in the z direction. The light is sequentially strobed by the computer 21 in the camera housing and observed by the cameras, and the results thereof are transmitted to a computer 27 which serves as a main computer in the system. Interconnecting wires and cables are conventional in nature, and are not shown. The information generated by the cameras and the computer in the housing is transmitted to the computer 28 and to an ultrasound scan screen device 30.

The foregoing calibration procedure establishes a space volume in the room 10 in which the medical procedure or study will take place. Orientation is correct in the X, Y and Z coordinates of the room regardless of the position of the camera unit 12 relative to the initial calibration of the cameras and the computer in the housing.

A probe 32 (FIGS. 3 and 4) is provided for locating the kidney stone or other concretion, or other bodily target. The probe 32 includes an ultrasound head 34 of known type, comprising an ultrasound sending unit that oscillates back and forth to provide a fan-shaped pattern, and also an ultrasound receiving transducer. The head 34 is mounted at the end of a handle 36, on which is mounted a mushroom shaped target 38 having a plurality radiation emitting devices comprising of infrared LEDs 40 mounted thereon in a pair of circles, relatively toward the bottom and the top of the mushroom. This shape is not essential, but is a very good one for our purpose. The infrared LEDs on the probe, and the cameras, are sequentially strobed by the small computer 21 to determine the position of the probe. A wire or cable 42 is provided for connecting the probe to the main computer 28 and the ultrasound scan screen device or apparatus 30. The LEDs are strobed by the main computer.

The ultrasound scan screen apparatus 30 includes three video display screens 44 (the X-Y or top view), 46 (the Y-Z side view) and 48 (the X-Z front view). The probe is indicated at 32 on each of the three screens, while the kidney stone or other concretion is indicated at 50. The probe is positioned against the skin of the patient in the general vicinity of the kidney stone, and the angle of the probe is moved until the probe is aligned with the stone as is indicated on the three screens 44, 46 and 48. The cutaway portion of the table 22 is shown at 52 on the video display screen 44.

Above the video display screens 44 and 46 are three numerical displays 54, 56, and 58 respectively for the X, Y and Z directions. No numerals are indicated in the drawing but numerals would appear in actual use as supplied by the computer 28 to indicate the distance the table would have to move in each of the three directions, namely X, Y and Z to place the stone precisely at the zero point as previously discussed. In addition, the ultrasound device is provided with a caliper feature, and this is well known in ultrasound devices. This allows the distance from the patient's skin to the stone to be measured precisely, and is shown on a display 60. The probe is shown in FIG. 4 as being pressed against the skin 62 of the patient, with the stone shown somewhat generically at 50 in the underlying bodily tissue 64.

In the present example where a kidney stone is located a lithotripter reflector is moved into position and pressed against the body of the patient to locate the external second focus point of the ellipsoidal reflector precisely on the kidney stone. The lithotripter is then operated as a known device, with shockwaves being generated in the reflector by a succession of sparks across a gap at the first focus point of the ellipsoidal reflector. As is known, the reflector is filled with water, and the shockwave is transmitted through the water and through the tissues of the body, which are mainly water, to focus on the kidney stone, and reduce it to fine particles which readily pass from the kidneys with the urine.

As noted, the invention is not limited to destruction of kidney stones, but can be used with other bodily concretions, such as gall stones. The apparatus of the invention also can be used to locate tumors, or to ascertain the precise position of a mending break in a bone so that the bone may be X-rayed to ascertain the state of healing of the bone.

The specific example of the invention as herein shown as described is for illustrative purposes only. Various changes will no doubt occur to those skilled in the art, and will be understood as forming a part of the present invention insofar as they fall within the spirit and scope of the appended claims.

The invention is claimed as follows:

1. Apparatus for locating a target in a human body comprising a three dimensional viewing camera unit including a housing, three cameras mounted in said housing in fixed relation to one another, and an auxiliary computer mounted in said housing, means for supporting said camera unit at an elevated location, a patient examining table disposed within respective aspects seen by said three cameras, said patient examining table being adapted to support a human patient having therein a target an ultrasound probe and an ultrasound scan screen apparatus, said probe having a plurality of radiation sources capable of being seen by said cameras, and a main computer, said auxiliary computer being electrically connected to said three cameras and to said main computer, said ultrasound probe being connected to said scan screen apparatus, said probe radiation sources being electrically connected to and strobed by said auxiliary computer, said ultrasound scan screen apparatus having three displays of X-Y, X-Z and Y-Z planes and being electrically connected to said probe to shown the relation of said probe to said target, and said ultrasound scan screen apparatus respectively having said three displays indicating a desired amount of movement of said patient examining table to position said target at a desired location.

2. Apparatus as set forth in claim 1 and further including a radiation source fixed relative to said said table, said table being moved to different horizontal and vertical positions in said room, and said fixed radiation source and said cameras being sequentially strobed by said auxilliary computer and the results stored in said main computer for orienting X, Y and Z coordinates to predetermine a working volume relative to a room in which said target locating device is installed.

3. A method of locating a target in a living body of a patient which comprises disposing a single electrically operated radiation emitting device in a fixed position relative to a patient examining table, moving said table and monitoring said radiation emitting device with three dimensional viewing camera means sensitive to the radiation emitted by said device, utilizing a first computer to control radiation from said device, storing information from said camera means in as second computer as to different positions of said radiation emitting device as it moves in fixed relation to said table upon movement of said table, placing said living body of a patient on said table and holding an ultrasonic probe in contact with said patient, said patient having a target therein, said probe having a plurality of electrically operated radiation emitting devices thereon, strobing said radiation emitting devices sequentially with said first computer to cause said radiation emitting devices to radiate in sequence, and monitoring the sequentially strobed probe radiation emitting devices with said three dimensional viewing camera means to detect the position of said probe, and determining the position of said probe relative to said target.

4. The method as set forth in claim 3 wherein said table with said single radiation emitting device is moved horizontally and vertically with said table maintaining a fixed relation to said single radiation emitting device to establish a volume within which said probe is to operate.

5. The method as set forth in claim 4 wherein said camera means is mounted in a room and the volume is defined in X, Y and Z coordinates relative to the room in which the camera means is installed.

6. The method as set forth in claim 3 wherein said three dimensional camera means comprises three cameras.

7. The method as set forth in claim 6 in which said three cameras are supplied as a factory calibrated unit including said first computer.

8. The method as set forth in claim 6 and further including moving said table with the patient therefrom to position said target in a desired location.

* * * * *